US012129231B2

(12) United States Patent
Fisher et al.

(10) Patent No.: US 12,129,231 B2
(45) Date of Patent: Oct. 29, 2024

(54) PROCESS AND APPARATUS FOR SCRUBBING A HYDROCARBON GAS STREAM

(71) Applicant: UOP LLC, Des Plaines, IL (US)

(72) Inventors: Aric G. Fisher, Tulsa, OK (US); Nickolas D. Kapaun, Chicago, IL (US); William J. Whyman, Collinsville, OK (US); James P. Glavin, Naperville, IL (US)

(73) Assignee: UOP LLC

( * ) Notice: Subject to any disclaimer, the term of this patent is extended or adjusted under 35 U.S.C. 154(b) by 62 days.

(21) Appl. No.: 17/966,787

(22) Filed: Oct. 15, 2022

(65) Prior Publication Data

US 2023/0212097 A1     Jul. 6, 2023

Related U.S. Application Data

(60) Provisional application No. 63/295,250, filed on Dec. 30, 2021.

(51) Int. Cl.
| | |
|---|---|
| *C07C 7/12* | (2006.01) |
| *B01D 53/047* | (2006.01) |
| *B01D 53/14* | (2006.01) |
| *C07C 7/00* | (2006.01) |

(52) U.S. Cl.
CPC ............. *C07C 7/12* (2013.01); *B01D 53/047* (2013.01); *C07C 7/005* (2013.01); *B01D 2253/10* (2013.01); *B01D 2256/24* (2013.01); *B01D 2259/402* (2013.01)

(58) Field of Classification Search
None
See application file for complete search history.

(56) References Cited

U.S. PATENT DOCUMENTS

| | | | | |
|---|---|---|---|---|
| 5,057,642 A | * | 10/1991 | Johnson | .............. C07C 7/12 585/820 |
| 8,252,255 B2 | * | 8/2012 | Estaba Sambrano | ............... C07D 249/06 95/135 |
| 2013/0330796 A1 | * | 12/2013 | Beck | ............... C12P 5/007 435/254.11 |
| 2016/0002672 A1 | * | 1/2016 | Beck | ............... C12P 5/007 435/254.11 |

* cited by examiner

*Primary Examiner* — Tam M Nguyen
(74) *Attorney, Agent, or Firm* — Paschall & Associates, LLC; James C. Paschall

(57) ABSTRACT

A process for adsorbing impurities from hydrocarbon gas streams is disclosed. The process involves passing a hydrocarbon gas stream and a solid dry adsorbent under inert environment to a scrubbing chamber for adsorbing impurities from the hydrocarbon gas streams within the scrubbing chamber. The process adsorption of impurities in scrubbing chamber is carried under non-oxidative conditions to generate a clean product gas.

20 Claims, 2 Drawing Sheets

PROCESS AND APPARATUS FOR SCRUBBING A HYDROCARBON GAS STREAM

CROSS-REFERENCE TO RELATED APPLICATIONS

This application claims priority from U.S. Provisional Application No. 63/295,250, filed Dec. 30, 2021, which is incorporated herein in its entirety.

FIELD

The field relates to the process for adsorbing impurities from hydrocarbon gas via scrubbing.

BACKGROUND

In many refining and gas processing applications, removal of acid gas components from a hydrocarbon gas stream is performed by scrubbing hydrocarbon gas with an aqueous caustic solution. Because the process stream comprises hydrocarbons, scrubbing is performed inside of closed pressure vessels. As the gas and liquids come into contact, chemical reactions take place by reacting the acid gas components with the caustic to make salts, which are non-volatile and water soluble, so leave with the aqueous phase. Eventually, all the caustic has been reacted to make salts and must be refreshed. Using liquid caustic allows for removal of spent caustic and addition of fresh caustic to the process without the risk of introducing air to the process or allowing hydrocarbon gas to escape from the process. As such, the scrubbing operation can run continuously by adding and withdrawing caustic solution as required.

A drawback of liquid scrubbing is that the caustic is diluted with a large quantity of fresh water, and the maximum caustic concentration is limited by the solubility of the caustic and salts present in the solution. This means that a makeup stream of clean, fresh water is required, and a similar amount of wastewater is generated. This wastewater contains trace hydrocarbons, as well as salts, and leftover caustic. For treatment of acid gas components in flue gas streams leaving combustion chambers, so-called dry scrubbing is often used. In dry scrubbing, the vapor stream is mixed directly with a solid adsorbent such as sodium bicarbonate which reacts with the acid gas components to make solid salts. The solid salts are easily withdrawn from the scrubbing chamber. The key difference of the flue gas streams from the hydrocarbon gas streams is that the flue gas streams have been combusted, so the hydrocarbon components have been oxidized to carbon oxides and water vapor. Moreover, the pressure of a flue gas stream is typically only slightly higher than atmospheric pressure. Introduction of the powdered sodium bicarbonate into the flue gas is performed by pneumatic conveying. The introduction of additional air poses no risk because the flue gas is already oxidized, and any flue gas leaving the system with the spent solid sodium bicarbonate also poses no flammability risk.

The known scrubbing technology does not have the ability to maintain a tight pressure and atmospheric barrier required to mitigate the risk of mixing hydrocarbon and air when either introducing fresh adsorbent or withdrawing the spent salts.

An improved scrubbing process for removing acid gas impurities from hydrocarbon gas streams is desired.

BRIEF SUMMARY

A process for adsorbing impurities from a hydrocarbon gas stream is presented. A solid adsorbent is passed under inert environment to a scrubbing chamber. The hydrocarbon gas stream is also passed to said scrubbing chamber. Impurities are adsorbed from the hydrocarbon gas stream in the scrubbing chamber under non-oxidative conditions to generate a clean product gas stream.

Additional details and embodiments of the disclosure will become apparent from the following detailed description of the disclosure.

DEFINITIONS

Figure 1:
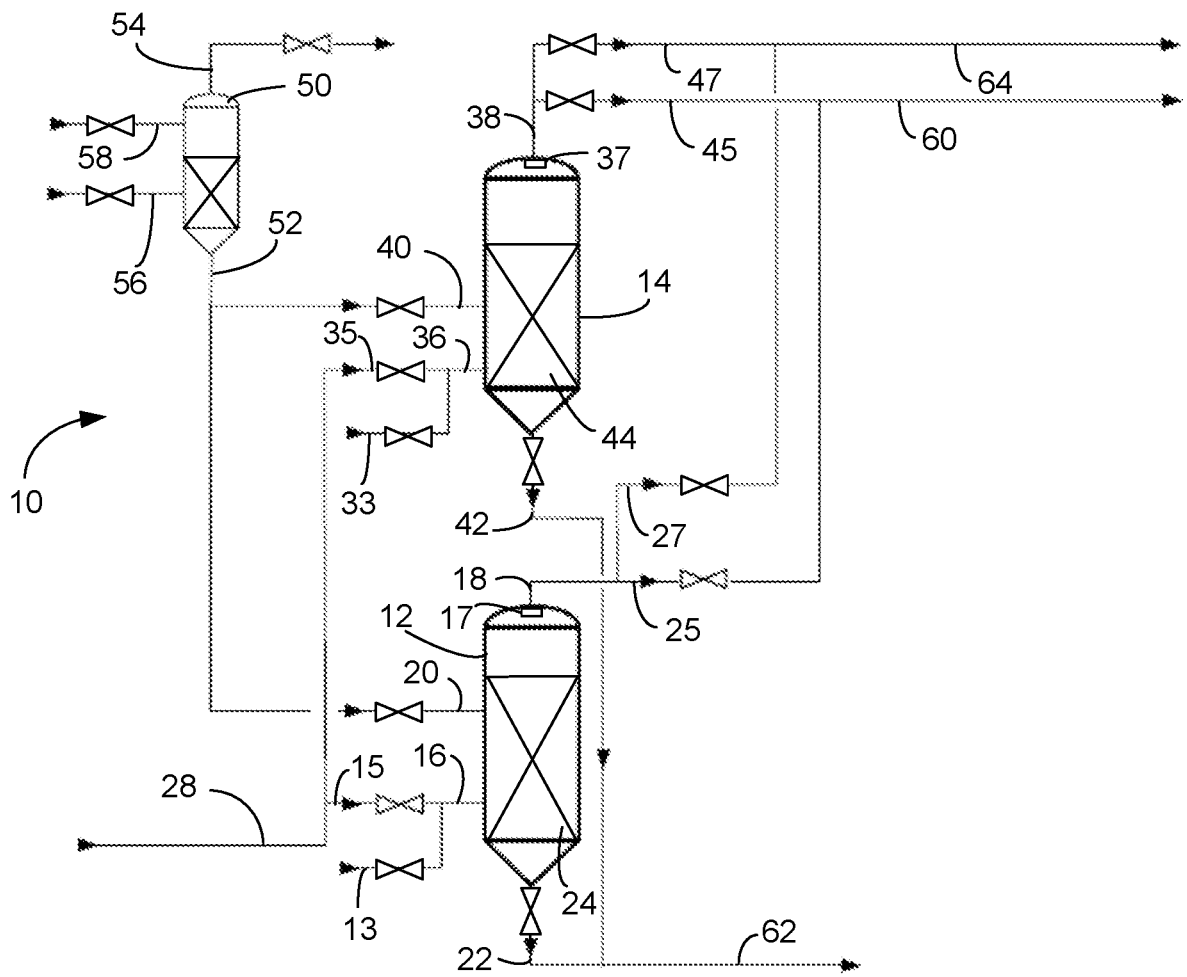
FIG. 1 is a schematic view of a process of the present disclosure.

The term "communication" means that fluid flow is operatively permitted between enumerated components, which may be characterized as "fluid communication". The term "communication" may also mean that data or signals are transmitted between enumerated components which may be characterized as "informational communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. A lock hopper is as separator that receives gas under atmospheric pressure. One or more valves to or from the hopper may be closed while leaving one inlet valve open in downstream communication with a gas stream at higher pressure to receive the gas stream at higher pressure to enable the hopper to be brought to a pressure that is different than atmospheric. Once pressurized, an outlet valve can be opened to discharge contents of the hopper.

As used herein, the term "predominant" or "predominate" means greater than 50%, suitably greater than 75% and preferably greater than 90%.

The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

DETAILED DESCRIPTION

This disclosure applies the advantages of dry scrubbing to a hydrocarbon stream at elevated pressure by the use of an inert gas lock hopper for fresh adsorbent addition to avoid introduction of air into the process. Also, parallel scrubbing chambers in alternating operating and recharging steps, or alternatively a unloading lock hopper separator, allows for hydrocarbon to be removed from the spent solids before unloading, preventing hydrocarbon from leaking to the atmosphere. Together, this allows for continuous gas scrubbing without use of water.

The present disclosure is a process for adsorbing impurities from a hydrocarbon gas stream. The impurities may be an acid gas such as hydrogen chloride or hydrogen sulfide found in a hydrocarbon gas stream. A solid dry adsorbent is passed to a scrubbing chamber under an inert environment. The solid dry adsorbent may have alkaline qualities and may be sodium bicarbonate. Other sodium or alkaline salts may be suitable. The inert environment should be an oxygen-free environment that may be provided by a nitrogen blanket. The hydrocarbon gas is passed to the scrubbing chamber in which the impurities from the hydrocarbon gas are adsorbed onto the adsorbent in the scrubbing chamber under non-oxidative or reducing conditions to generate a clean product gas. Specifically, the acid gas components in the hydrocarbon gas stream react with the alkaline component in the adsorbent to remove the acid gas component from the hydrocarbon gas stream and produce a salt.

The hydrocarbon gas may comprise methane, $C_{2+}$ hydrocarbons, nitrogen, oxygen, water, carbon oxides and acid gas. Acid gas removal can reach about 95 to about 99 wt % and can leave only about 1 wt % to 1000 wppm acid gas components in the clean hydrocarbon stream. The alkaline adsorbent may be sodium bicarbonate. The acid gas reaction with the sodium bicarbonate can produce carbon oxides and sodium salts such as sodium chloride or sodium sulfide.

Impurities such as hydrogen chloride may be generated in a plastics pyrolysis process, a reforming, dehydrogenation or isomerization process with a chloride containing catalyst. Hydrogen sulfide may be present in hydrocarbon streams generated by hydroprocessing hydrocarbon streams containing organic sulfur in a refinery.

Two ways to practice this invention are described. In both cases, all control valves in the process would ideally be controlled by an automatic control system, which could also receive signals from instrumentation including for example, flowmeters, pressure transmitters, online gas analyzers, etc. for feedback of the process conditions.

In both cases, the system could operate at any pressure, so long as it is sufficiently high enough such that the product gas and purge gas can flow by pressure above atmospheric, such as 70 kPa (g) (10 psig) to 350 kPa (g) (50 psig), through the system to their respective destinations. The system ideally operates at a temperature sufficiently above the process gas dewpoint such that none of the components condense. Heaters on the inert gas stream and/or feed streams could be used to ensure the proper temperature is met.

The present process may be performed by passing adsorbent to a first scrubbing chamber 12 and a second scrubbing chamber 14 in a swing bed arrangement 10 shown in FIG. 1. The swing bed arrangement 10 comprises the first scrubbing chamber 12 and the second scrubbing chamber 14. The first scrubbing chamber 12 is a vessel connected with a first gas inlet line 16 for charging gas to the chamber, a first gas outlet line 18 extending from an overhead of the chamber for discharging gas from the chamber, a first solid inlet line 20 for adding solid adsorbent to the chamber and a first solid outlet line 22 extending from a bottom of the chamber for removing solid adsorbent from the chamber. A first filter 17 prevents solids from exiting in the first gas outlet line 18. The first gas inlet line 16 may be fed by a hydrocarbon gas stream with impurities from a first hydrocarbon feed gas line 15 or a first inert gas supply line 13. The inert gas may be nitrogen. The first gas outlet line 18 may feed a first product gas line 25 or a first purge gas line 27. The first product gas line 25 feeds a product gas recovery line 60, while the first purge gas line 27 feeds a purge collection line 64. The first solid outlet line 22 feeds a spent solids recovery line 62.

The second scrubbing chamber 14 is a vessel connected with a second gas inlet line 36 for charging gas to the chamber, a second gas outlet line 38 extending from an overhead of the chamber for discharging gas from the chamber, a second solid inlet line 40 for adding solid adsorbent to the chamber and a second solid outlet line 42 extending from a bottom of the chamber for removing solid adsorbent from the chamber. A second filter 37 prevents solids from exiting in the second gas outlet line 38. The second gas inlet line 36 may be fed by hydrocarbon gas with impurities from a second hydrocarbon feed gas line 35 or a second inert gas supply line 33. The inert gas may be nitrogen. The second gas outlet line 38 may feed a second product gas line 45 or a second purge gas line 47. The second product gas line 45 feeds the product gas recovery line 60, while the second purge gas line feeds the purge collection line 64. The second solid outlet line feeds the spent solids recovery line 62.

When active, the first scrubbing chamber is partially filled with solid adsorbent powder 24. The inlet hydrocarbon gas from a hydrocarbon gas line 28 comprising hydrocarbon gas with acid gas components is admitted through an open control valve on the first hydrocarbon gas feed line 15 which feeds the first gas inlet line 16 and enters the first scrubbing chamber 12. In the scrubbing chamber, the hydrocarbon gas mixes with solid adsorbent 24 in a fluidized solid phase and neutralizing reactions take place that react acid gas components with solid caustic to create solid salts. Oxygen in air is not admitted to the first scrubbing chamber 12, so the adsorption takes place under non-oxidative, perhaps reducing conditions. A clean hydrocarbon gas stream, free of acid gas impurities, exits the first scrubbing chamber 12 through the first filter 17 in the top of the first scrubbing chamber 12 to remove any entrained solids. The clean hydrocarbon gas may exit the first scrubbing chamber through the first gas outlet line 18 extending from an overhead of the scrubbing chamber 12 through an open control valve on the first product gas line 25 to a product gas recovery line 60.

When active, the second scrubbing chamber 14 is partially filled with solid adsorbent powder 44. The inlet hydrocarbon gas from a hydrocarbon gas line 28 comprising hydrocarbon gas with acid gas components is admitted through an open control valve on the second hydrocarbon gas feed line 35 which feeds the second gas inlet line 36 and enters the second scrubbing chamber 14. In the scrubbing chamber, the hydrocarbon gas mixes with solid adsorbent 44 in a fluidized solid phase and neutralizing reactions take place that react acid gas components with solid caustic to create solid salts. Oxygen in air is not admitted to the second scrubbing chamber 14, so the adsorption takes place under non-oxidative, perhaps reducing conditions. A clean hydrocarbon gas stream, free of acid gas impurities, exits the second scrubbing chamber 14 through the second filter 37 in the top of the second scrubbing chamber to remove any entrained solids. The clean hydrocarbon gas may exit the second scrubbing chamber 14 through the second gas outlet line 38 extending from an overhead of the scrubbing chamber through an open control valve on the second product gas line 45 to a product gas recovery line 60.

An adsorbent loader 50 is also provided for loading solid adsorbent into the scrubbing chambers 12 and 14 through a solid loading line 52. The adsorbent loader 50 also includes an adsorbent supply line 56 and an inert gas supply line 58. The inert gas may be nitrogen. When the adsorbent loader is empty, it may be open to the atmosphere through a vent line 54 with an open control valve thereon. To refill the adsorbent loader 50 the control valve on the adsorbent supply line 56 is opened to allow adsorbent to flow into the loader 50. The vent 54 may still be open at this point. Once, the loader 50 is loaded with adsorbent, the control valve on the adsorbent supply line 56 may be closed and a control valve on an inert gas supply line 58 may be opened along with the control valve on the vent line 54 to pass inert gas such as nitrogen to the loader 50 to purge the loader 50 of oxygen in air. Loading the adsorbent loader 50 should be performed when either the first scrubbing chamber 12 or the second scrubbing chamber 14 is actively adsorbing impurities from the hydrocarbon gas stream, so there is no interruption in service. When the purge step is finished, all control valves on lines 20, 40, 54, 56, 58 should be closed until such time for loading one of the scrubbing chambers with adsorbent.

While the first scrubbing chamber 12 is still actively scrubbing the hydrocarbon gas, the second scrubbing chamber 14 that was formerly but not currently in operation may be purged of hydrocarbon by opening the control valve on the second inert gas supply line 33 and the second purge gas line 47 and closing all the other control valves on lines to or from the second scrubbing chamber 14. The inert gas is fed to the second scrubbing chamber 14 while it is inactive to purge all remaining hydrocarbons from the chamber. Purged gas and inert gas from the second purge gas line 47 are collected in the purge gas collection line 64 and may be routed to gas disposal, such as by flare, a process destination or to a thermal oxidizer.

Once completely purged of hydrocarbons, the control valves on the second inert gas supply line 33 and the second purge gas line 47 are closed and the control valve on the second solid outlet line 42 is opened to permit the spent adsorbent to discharge into a spent solid recovery line 62. Spent solids transport can be facilitated by inert gas or mechanical conveyance. The inactive, second scrubbing chamber 14 would now be empty and under nitrogen atmosphere. Meanwhile, the loader 50 is full of adsorbent under a nitrogen blanket. The spent solids from line 62 may be bagged for storage and perhaps recovery.

The second scrubbing chamber 14 is now ready to be reloaded. The control valve on the second solids outlet line 42 is closed and the control valve on the second solid inlet line 40 is opened to enable the fresh adsorbent to be transferred from the loader 50 to the second scrubbing chamber 14 by inert gas or mechanical conveyance. When the adsorbent is loaded into the second scrubbing chamber 14, all the control valves on lines to and from the second scrubbing chamber 14 are closed. The chamber is now recharged and can remain on standby until needed. The adsorbent loader 50 can also be refilled at this time.

Ascertaining that the adsorbent 24 in the active first scrubbing chamber 12 is spent can be detected by breakthrough of acid gas components or predicted by the estimated adsorbent life use, chamber capacity, and flow rates. When the adsorbent is spent, the gas flow can be switched to the standby second scrubbing chamber 14, and the active first scrubbing chamber 12 taken offline to be recharged. To do so, the control valves on the hydrocarbon gas feed line 35 and the product gas line 45 are opened to enable the hydrocarbon gas stream to initiate flow to the second scrubbing chamber 12 to contact fresh adsorbent and clean product gas flow in the product gas line 45 to the product gas recovery line 60. Typically, but not necessarily, afterward, all of the control valves on lines to and from the first scrubbing chamber 12 are closed, so flow of the hydrocarbon gas stream to the first scrubbing chamber 12 through the first gas inlet line 16 is terminated.

While the second scrubbing chamber 14 is actively scrubbing the hydrocarbon gas, the first scrubbing chamber 12 that was formerly but not currently in operation may be purged of hydrocarbon by opening the control valve on the first inert gas supply line 13 and the first purge gas line 27 and closing all the other control valves on lines to or from the first scrubbing chamber 14. The inert gas is fed to the first scrubbing chamber 12 while it is inactive to purge all remaining hydrocarbons from the chamber. Purged gas and inert gas from the first purge gas line 27 are collected in the purge gas collection line 64 and may be routed to gas disposal, such as by flare, a process destination or to a thermal oxidizer.

Once completely purged of hydrocarbons, the control valves on the first inert gas supply line 13 and the first purge gas line 27 are closed and the control valve on the first solid outlet line 22 is opened to permit the spent adsorbent to discharge into a spent solid recovery line 62. Spent solids transport can be facilitated by inert gas or mechanical conveyance. The inactive, first scrubbing chamber 12 would now be empty and under nitrogen atmosphere. Meanwhile, the loader 50 is full of adsorbent under a nitrogen blanket. The spent solids from line 62 may be bagged for storage and perhaps recovery.

The first scrubbing chamber 12 is now ready to be reloaded. The control valve on the first solids outlet line 22 is closed and the control valve on the first solid inlet line 20 is opened to enable the fresh adsorbent to be transferred from the loader 50 to the first scrubbing chamber 14 by inert gas or mechanical conveyance. When the adsorbent is loaded into the first scrubbing chamber 12, all the control valves on lines to and from the first scrubbing chamber 12 are closed. The chamber is now recharged and can remain on standby until needed. The adsorbent loader 50 can also be refilled at this time.

When the adsorbent 24 in the active second scrubbing chamber 14 is spent which can be ascertained as previously mentioned, the gas flow can be switched to the standby first scrubbing chamber 12, and the active second scrubbing chamber 14 taken offline to be recharged. To do so, the control valves on the hydrocarbon gas feed line 15 and the product gas line 25 are opened to enable the hydrocarbon gas stream to initiate flow to the second scrubbing chamber 14 to contact fresh adsorbent and clean product gas flow in the product gas line 25 to the product gas recovery line 60. Typically, but not necessarily, afterward, all of the control valves on lines to and from the second scrubbing chamber 14 are closed, so flow of the hydrocarbon gas stream to the second scrubbing chamber 14 through the second gas inlet line 36 is terminated.

The steps of purging, emptying and refilling the second scrubbing chamber 14 can take place at this point when the first scrubbing chamber 12 is purifying hydrocarbon gas, so no interruption in service occurs. Accordingly, when adsorbent in the second scrubbing chamber 14 is spent, the flow of hydrocarbon gas to the first scrubbing chamber 12 can be reinitiated.

Figure 2:
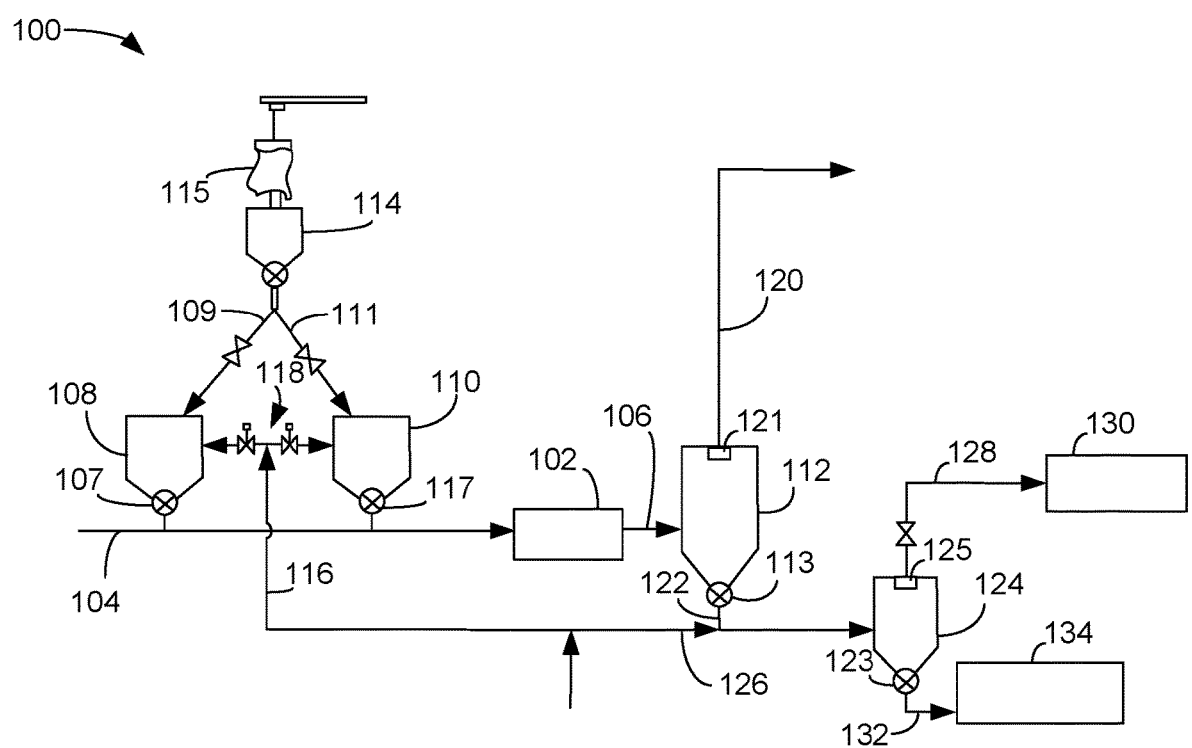
FIG. 2 is a schematic view of an alternative process of the present disclosure.

FIG. 2 depicts an arrangement 100 in which solid adsorbent is continuously passed to a single scrubbing chamber 102. In this arrangement 100, the hydrocarbon gas containing the acid gas impurities in a hydrocarbon gas line 104 is continuously charged to the single scrubbing chamber 102. The scrubbing chamber 102 comprises a vessel with an inlet for receiving hydrocarbon gas containing acid gas components and entrained solid adsorbent from line 104 and an outlet for scrubbed hydrocarbon gas and spent adsorbent in an outlet line 106.

Dry, solid adsorbent is added continuously to the chamber using two lock hopper loaders, a first loader 108 and a second loader 110 that are alternatively filled with solid adsorbent under an inert atmosphere. The contaminated hydrocarbon gas in hydrocarbon gas line 104 carries the solid adsorbent dropped into the hydrocarbon gas stream in the hydrocarbon gas line 104 from the first lock hopper loader 108 or the second lock hopper loader 110 into the scrubbing chamber 102 under an inert environment, absent the presence of air. Alternatively, an inert gas stream may be used to carry the solid adsorbent to the scrubbing chamber 102. The hydrocarbon gas line 104 is a conduit for transporting the hydrocarbon gas stream. In the scrubbing chamber 102 neutralizing reactions take place in a fluidized solid dilute phase that react acid gas components with solid alkaline adsorbent to create solid salts in a non-oxidative, reducing environment to create a clean hydrocarbon product gas stream. The clean hydrocarbon product gas and spent adsorbent exit the scrubbing chamber 102 in the outlet line 106 and enter a first separator 112. The first separator 112 is in downstream communication with the scrubbing chamber 102.

The two adsorbent lock hopper loaders 108 and 110 alternate feeding the hydrocarbon gas line 104 to ensure a supply of adsorbent is constantly entering the hydrocarbon gas stream. While the first loader 108 is actively feeding adsorbent to the line 104 and to the scrubbing chamber 102 through an open first loader valve 107 at the bottom of the loader, the second loader 110 is on standby. While the second loader 110 is actively feeding adsorbent to the line 104 and to the scrubbing chamber 102 through an open second loader valve 117 at the bottom of the loader, the first loader 108 is on standby. The loader 108, 110 on standby is refilled with adsorbent from a common hopper 114 under air with the valve 107, 117 closed. The common hopper 114 loads the first loader 108 by a first hopper line 109 through a control valve thereon and the second loader 110 by a second hopper line 111 through a control valve thereon. The common hopper 114 may be loaded with bags 115 of adsorbent. Other methods for loading the common hopper 114 are also possible such as loading from storage silo or truck.

Once filled with adsorbent, the loader 108, 110 is purged with an inert gas from line 116 to purge oxygen from the loader. The inert gas may be nitrogen and vent to atmosphere. Manifold 118 ensures that inert gas from line 116 is directed to the appropriate standby loader 108, 110. Once the active loader 108, 110 is near empty of adsorbent, its passing adsorbent to the hydrocarbon gas line 104 is terminated by closing the valve 107 at the bottom of the loader 108, 110, and the standby loader 110, 108 initiates passing solid adsorbent to the hydrocarbon line 104 and to the scrubbing chamber 102 by opening the valve 117 at the bottom of the loader 110, 108. While the formerly standby loader 110, 108 is initiated into active operation, the formerly active loader 108, 110 is refilled with adsorbent as described.

In the first separator 112, the spent solids are removed from the product gas stream and are collected in the bottom of the first separator 112. The separated clean product gas stream is taken in a product gas line 120 extending from an overhead of the first separator 112 to product recovery in a fluidized dense phase. A filter 121 in the top of the first separator 112 prevents solids from leaving the first separator through the product gas line 120 in the overhead. Periodically, a valve 113 at a bottom of the first separator 112 opens and the solids are conveyed through a bottoms line 122 with inert gas and/or mechanical means into a second separator 124.

The second separator 124 may be a lock hopper. An inert gas from line 126 may assist flow in the bottoms line 122 to the second separator and sweep hydrocarbon gas from spent adsorbent in the second separator 124. The hydrocarbon and inert gas mixture flows through a filter 125 to remove any entrained solids, and then is routed in line 128 to gas disposal 130 which may comprise, for example, a flare, a process destination, or a thermal oxidizer. Once the second separator is purged free of hydrocarbon, a valve on the overhead line 128 is closed and a valve 123 at a bottom of the second separator 124 is opened and the spent adsorbent is conveyed through a bottoms line 132 from the second separator 124 to a spent solids disposal apparatus. For example, the spent adsorbent may be packaged in bags for storage, transport and/or rejuvenation.

The second separator 124 and the surge capacity for adsorbent in the scrubbing chamber 102 should be sized to enable the second separator to remove spent solids at least as quickly as they are accumulated in the chamber, allowing for uninterrupted operation.

The disclosed process enables removal of impurities such as acid gases from a hydrocarbon without use of liquid that must be cleaned or disposed of while keeping oxygen away from the hydrocarbon gas.

Specific Embodiments

While the following is described in conjunction with specific embodiments, it will be understood that this description is intended to illustrate and not limit the scope of the preceding description and the appended claims.

A first embodiment of the disclosure is a process for adsorbing impurities from a hydrocarbon gas stream comprising passing a solid adsorbent under an inert environment to a scrubbing chamber; passing the hydrocarbon gas stream to the scrubbing chamber; adsorbing impurities from the hydrocarbon gas stream in the scrubbing chamber under non-oxidative conditions to generate a clean product gas stream. An embodiment of the disclosure is one, any or all of prior embodiments in this paragraph up through the first embodiment in this paragraph wherein an inert gas stream is supplied to the scrubbing chamber for creating the inert environment. An embodiment of the disclosure is one, any or all of prior embodiments in this paragraph up through the first embodiment in this paragraph wherein the step of passing the solid adsorbent to the scrubbing chamber is a continuous process. An embodiment of the disclosure is one, any or all of prior embodiments in this paragraph up through the first embodiment in this paragraph wherein the step of passing the solid adsorbent to the scrubbing chamber is a swing bed process. An embodiment of the disclosure is one, any or all of prior embodiments in this paragraph up through the first embodiment in this paragraph wherein the hydrocarbon gas stream is mixed with the solid adsorbent and the hydrocarbon gas stream carries the adsorbent to the scrubbing chamber. An embodiment of the disclosure is one, any or all of prior embodiments in this paragraph up through the first embodiment in this paragraph wherein the scrubbing chamber is a first scrubbing chamber and further comprising a second scrubbing chamber supplied with the solid adsorbent under an inert environment to purge gases from the second scrubbing chamber and recovering remaining clean product gas stream from an overhead line of the second scrubbing chamber. An embodiment of the disclosure is one, any or all of prior embodiments in this paragraph up through the first embodiment in this paragraph further comprises recovering spent solid adsorbent from a bottom of the secondary scrubbing chamber and the clean product gas stream is recovered from the overhead line of the first scrubbing chamber. An embodiment of the disclosure is one, any or all of prior embodiments in this paragraph up through the first embodiment in this paragraph wherein the step of recovering the solid adsorbent from the second scrubbing chamber takes place when the second scrubbing chamber is inactive.

A second embodiment of the disclosure is a process for adsorbing impurities from a hydrocarbon gas stream comprising passing the hydrocarbon gas stream to a first scrubbing chamber comprising an adsorbent; adsorbing impurities from the hydrocarbon gas stream onto the adsorbent in the first scrubbing chamber under non-oxidative conditions; passing an adsorbent under an inert environment to a second scrubbing chamber; terminating flow of the hydrocarbon gas stream to the first scrubbing chamber; initiating flow of the hydrocarbon gas stream to the second scrubbing chamber; and adsorbing impurities from the hydrocarbon gas stream onto the adsorbent in the second scrubbing chamber under nonoxidative conditions. An embodiment of the disclosure is one, any or all of prior embodiments in this paragraph up through the second embodiment in this paragraph further comprising purging hydrocarbons from the first scrubbing chamber after terminating flow of the hydrocarbon gas stream to the first scrubbing chamber. An embodiment of the disclosure is one, any or all of prior embodiments in this paragraph up through the second embodiment in this paragraph further comprising recovering spent adsorbent from the first scrubbing chamber after purging hydrocarbons from the first scrubbing chamber. An embodiment of the disclosure is one, any or all of prior embodiments in this paragraph up through the second embodiment in this paragraph further comprising refilling the first scrubbing chamber with a fresh adsorbent under an inert atmosphere after removing the spent adsorbent from the first scrubbing chamber. An embodiment of the disclosure is one, any or all of prior embodiments in this paragraph up through the second embodiment in this paragraph further comprising feeding adsorbent to the first scrubbing chamber from a loader under an inert atmosphere. An embodiment of the disclosure is one, any or all of prior embodiments in this paragraph up through the second embodiment in this paragraph further comprising reinitiating passing the hydrocarbon gas stream to the first scrubbing chamber comprising an adsorbent.

A third embodiment of the disclosure is a process for supplying solid adsorbent for adsorbing impurities from a hydrocarbon gas stream comprising passing a solid adsorbent to an adsorbent loader under an inert environment; passing the solid adsorbent from the adsorbent loader to a scrubbing chamber under an inert environment; passing the hydrocarbon gas stream to the scrubbing chamber; and adsorbing impurities from the hydrocarbon gas stream in the scrubbing chamber under non-oxidative conditions to generate a clean product gas stream. An embodiment of the disclosure is one, any or all of prior embodiments in this paragraph up through the third embodiment in this paragraph further comprising passing spent adsorbent and clean product gas stream from the scrubbing chamber to a separator and recovering clean product gas stream from an overhead of the separator and spent adsorbent from a bottom of the separator. An embodiment of the disclosure is one, any or all of prior embodiments in this paragraph up through the third embodiment in this paragraph further comprising passing the solid adsorbent from the adsorbent loader to the scrubbing chamber entrained in the hydrocarbon gas stream passing through a conduit. An embodiment of the disclosure is one, any or all of prior embodiments in this paragraph up through the third embodiment in this paragraph wherein the adsorbent loader is a first adsorbent loader and further comprising passing a solid adsorbent to a second adsorbent loader under an inert environment; terminating passing the solid adsorbent from the first adsorbent loader to the scrubbing chamber and initiating passing the solid adsorbent from the second adsorbent loader to the scrubbing chamber when the first adsorbent loader is empty. An embodiment of the disclosure is one, any or all of prior embodiments in this paragraph up through the third embodiment in this paragraph wherein the first adsorbent loader is refilled with fresh solid adsorbent. An embodiment of the disclosure is one, any or all of prior embodiments in this paragraph up through the third embodiment in this paragraph wherein the separator is a first separator and further comprising feeding the spent adsorbent from the first separator to a second separator under an inert environment and recovering purge gas stream from an overhead of the separator and recovering spent adsorbent from a bottom of the second separator.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for adsorbing acid gas impurities from a hydrocarbon gas stream comprising:
   passing a solid adsorbent under an inert environment to a scrubbing chamber;
   passing the hydrocarbon gas stream to said scrubbing chamber;
   adsorbing acid gas impurities from said hydrocarbon gas stream in said scrubbing chamber under non-oxidative conditions to generate a clean product gas stream.

2. The process of claim 1 wherein an inert gas stream is supplied to the scrubbing chamber for creating the inert environment.

3. The process of claim 1 wherein the step of passing the solid adsorbent to the scrubbing chamber is a continuous process.

4. The process of claim 1 wherein the step of passing the solid adsorbent to the scrubbing chamber is a swing bed process.

5. The process of claim 1 wherein the hydrocarbon gas stream is mixed with the solid adsorbent and the hydrocarbon gas stream carries the adsorbent to said scrubbing chamber.

6. The process of claim 1 wherein said scrubbing chamber is a first scrubbing chamber and further comprising a second scrubbing chamber supplied with said solid adsorbent under an inert environment to purge gases from said second scrubbing chamber and recovering a remaining clean product gas stream from an overhead line of said second scrubbing chamber.

7. The process of claim 6 further comprises recovering spent solid adsorbent from a bottom of said secondary scrubbing chamber and said clean product gas stream is recovered from said overhead line of said first scrubbing chamber.

8. The process of claim 7 wherein said step of recovering said solid adsorbent from said second scrubbing chamber takes place when said second scrubbing chamber is inactive.

9. A process for adsorbing acid gas impurities from a hydrocarbon gas stream comprising:
passing the hydrocarbon gas stream to a first scrubbing chamber comprising an adsorbent;
adsorbing impurities from said hydrocarbon gas stream onto said adsorbent in said first scrubbing chamber under non-oxidative conditions;
passing an adsorbent under an inert environment to a second scrubbing chamber;
terminating flow of the hydrocarbon gas stream to said first scrubbing chamber;
initiating flow of the hydrocarbon gas stream to said second scrubbing chamber; and
adsorbing acid gas impurities from said hydrocarbon gas stream onto said adsorbent in said second scrubbing chamber under nonoxidative conditions.

10. The process of claim 9 further comprising purging hydrocarbons from said first scrubbing chamber after terminating flow of the hydrocarbon gas stream to said first scrubbing chamber.

11. The process of claim 10 further comprising recovering spent adsorbent from said first scrubbing chamber after purging hydrocarbons from said first scrubbing chamber.

12. The process of claim 11 further comprising refilling said first scrubbing chamber with a fresh adsorbent under an inert atmosphere after removing said spent solid adsorbent from said first scrubbing chamber.

13. The process of claim 12 further comprising feeding adsorbent to said first scrubbing chamber from a loader under an inert atmosphere.

14. The process of claim 12 further comprising reinitiating passing the hydrocarbon gas stream to said first scrubbing chamber comprising an adsorbent.

15. A process for supplying solid adsorbent for adsorbing acid gas impurities from a hydrocarbon gas stream comprising:
passing a solid adsorbent to an adsorbent loader under an inert environment;
passing said solid adsorbent from said adsorbent loader to a scrubbing chamber under an inert environment;
passing the hydrocarbon gas stream to said scrubbing chamber; and
adsorbing acid gas impurities from said hydrocarbon gas stream in said scrubbing chamber under non-oxidative conditions to generate a clean product gas stream.

16. The process of claim 15 further comprising passing spent adsorbent and clean product gas stream from said scrubbing chamber to a separator and recovering clean product gas stream from an overhead of said separator and spent adsorbent from a bottom of said separator.

17. The process of claim 15 further comprising passing said solid adsorbent from said adsorbent loader to said scrubbing chamber entrained in said hydrocarbon gas stream passing through a conduit.

18. The process of claim 15 wherein the adsorbent loader is a first adsorbent loader and further comprising passing a solid adsorbent to a second adsorbent loader under an inert environment; terminating passing said solid adsorbent from said first adsorbent loader to said scrubbing chamber and initiating passing said solid adsorbent from said second adsorbent loader to said scrubbing chamber.

19. The process of claim 18 wherein said first adsorbent loader is refilled with fresh solid adsorbent.

20. The process of claim 16 wherein the separator is a first separator and further comprising feeding said spent adsorbent from said first separator to a second separator under an inert environment and recovering purge gas stream from an overhead of said separator and recovering spent adsorbent from a bottom of said second separator.

* * * * *